United States Patent
Benton (10) Patent No.: US 9,621,628 B1
(45) Date of Patent: Apr. 11, 2017

(54) MOBILE IMAGE CAPTURE AND TRANSMISSION OF DOCUMENTS TO A SECURE REPOSITORY

(71) Applicant: EA Holdings, Inc., Norcross, GA (US)

(72) Inventor: Melinda Heeth Benton, Celebration, FL (US)

(73) Assignee: EA Holdings, Inc., Norcross, GA (US)

( * ) Notice: Subject to any disclaimer, the term of this patent is extended or adjusted under 35 U.S.C. 154(b) by 105 days.

(21) Appl. No.: 14/033,160

(22) Filed: Sep. 20, 2013

Related U.S. Application Data (60) Provisional application No. 61/703,968, filed on Sep. 21, 2012.

(51) Int. Cl.
*H04L 29/08* (2006.01)
*H04L 9/00* (2006.01)

(52) U.S. Cl.
CPC ............... *H04L 67/06* (2013.01); *H04L 9/00* (2013.01)

(58) Field of Classification Search
CPC combination set(s) only.
See application file for complete search history.

(56) References Cited

U.S. PATENT DOCUMENTS

| | | | |
|---|---|---|---|
| 2001/0007983 A1* | 7/2001 | Lee | G06Q 20/04 705/69 |
| 2002/0077944 A1* | 6/2002 | Bly et al. | 705/35 |
| 2005/0097046 A1* | 5/2005 | Singfield | G06Q 20/042 705/42 |
| 2009/0185241 A1* | 7/2009 | Nepomniachtchi | 358/474 |
| 2010/0057614 A1* | 3/2010 | Rainey | G06Q 20/10 705/42 |
| 2010/0082470 A1* | 4/2010 | Walach | G06Q 20/0425 705/35 |
| 2010/0318461 A1* | 12/2010 | Smith | G06Q 20/042 705/43 |
| 2011/0091092 A1* | 4/2011 | Nepomniachtchi | G06K 9/3275 382/139 |
| 2011/0134248 A1* | 6/2011 | Heit | G06Q 20/04 348/161 |
| 2011/0205153 A1* | 8/2011 | Ueda et al. | 345/156 |
| 2012/0290643 A1* | 11/2012 | Fok Ah Chuen | H04W 4/02 709/203 |
| 2013/0097076 A1* | 4/2013 | Love | G06Q 20/0425 705/42 |

(Continued)

*Primary Examiner* — Taghi Arani
*Assistant Examiner* — Phy Anh Vu
(74) *Attorney, Agent, or Firm* — Thomas | Horstemeyer LLP; Randy R. Schoen

(57) ABSTRACT

Various methods and systems are provided for capture and transmission of images to a secure repository. In one example, among others, a method includes capturing an image of a document as an image file using a mobile device, adding metadata to the image file, and securely transmitting the image file to a server. The image file can be stored in a secure repository. In another example, a mobile device includes a secure transfer application that causes the mobile device to capture an image as an image file, add metadata to the image file, and transmit the image file to a server via a secure connection. The server may store the image file in a secure repository. In another example, a non-transitory computer-readable medium includes a program that captures an image, adds metadata to the image file, and transmits the image file securely to a server.

15 Claims, 11 Drawing Sheets

(56) References Cited

U.S. PATENT DOCUMENTS

| | | | |
|---|---|---|---|
| 2013/0198069 A1* | 8/2013 | Latimer | G06Q 20/042 |
| | | | 705/42 |
| 2013/0198071 A1* | 8/2013 | Jurss | G06Q 20/108 |
| | | | 705/42 |
| 2014/0270461 A1* | 9/2014 | Narendra | G06Q 20/0425 |
| | | | 382/137 |

* cited by examiner

MOBILE IMAGE CAPTURE AND TRANSMISSION OF DOCUMENTS TO A SECURE REPOSITORY

CROSS-REFERENCE TO RELATED APPLICATIONS

This application claims the benefit of U.S. Provisional Application No. 61/703,968, filed Sep. 21, 2012, the entire contents of which is hereby incorporated herein by reference.

BACKGROUND

In general, healthcare institutions have large volumes of medical records containing protected health information (PHI). Insurance companies, government agencies, educational institutions and other medical groups need access to these records to verify billing, check compliance, monitor quality and conduct research. Current methods of transmitting these records are inefficient, unsecure and cost-intensive. Many transmittal processes still rely on outmoded technologies such as email, postal mail and fax.

SUMMARY

Embodiments of the present disclosure are related to automated document capture and secure transmittal and more particularly, to methods and systems for document image capture and secure transmittal using mobile devices. In accordance with various embodiments, methods and systems for document image capture on a mobile communication device are provided such that the image is optimized and enhanced for data extraction from the document as depicted. These methods and systems may comprise capturing an image of a document using a mobile communication device; adding metadata to the image file; transmitting the image securely to a server; and archiving the image in the secure repository for later retrieval. Additionally, these methods and systems may comprise capturing a first image of a document using the mobile communication device; automatically detecting the document within the image; geometrically correcting the image; binarizing the image; correcting the orientation of the image; correcting the size of the image; and outputting the resulting image of the document.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Disclosed herein are various embodiments of methods related to automated document capture and secure transmittal. Reference will now be made in detail to the description of the embodiments as illustrated in the drawings, wherein like reference numbers indicate like parts throughout the several views.

A software program or application (or "app") may be executed by processing capabilities of a mobile device such as, e.g., a smart phone, tablet, personal digital assistant (PDA), or other appropriate mobile device. When executed by the model device, the application verifies the identity of the user through the use of, e.g., a username and password. In other embodiments, the user identity may be verified using movement patterns on an interactive display of the mobile device or by other biometric measurements. Once the user has logged in, the application allows the user to initiate document capture by providing a form on which the user can enter metadata pertinent to the document such as patient name or image type. In some cases, the metadata may be entered through a visual input such as, e.g., a quick response (QR) code. The user enters data and, when the form is completed, is directed to a capture page where the view through a built-in camera of the mobile device is displayed. The user orients the camera to provide the best image quality and presses an on-screen button to capture the document image. The user then reviews the image and if necessary may discard the image and then take another picture of the document. Once the user is satisfied with the image quality, the image can be saved to an encrypted storage or memory on the file system of the mobile device.

In some cases, the user may capture images of one or more documents and save them to a secure encrypted storage on the mobile device. By storing the images in the secure encrypted storage, the document images are not visible to the operating system of the mobile device and may only be viewed by the user once their credentials are verified and they are logged-in to the application. Thus, the user may create a collection of documents for transmission to a secure repository on a remote server. Once images of the documents are captured and annotated with metadata, the user may "save" the scanned images to the secure geographically-remote repository. A "save images" icon may be provided on the mobile device for the user.

Once the "save images" button is pressed on the touch screen, an SSL-encrypted connection can be opened to the remote server. The connection may be, e.g., a cellular link, WiFi link, Bluetooth link, or other wireless or wired communication link. The application may check for connectivity before transmission is initiated. After the communication link has been verified, the document images are transmitted using, e.g., a messaging format, which provides for data validation. After the remote server accepts the images, multiple copies of the document images may be stored on redundant storage media and notice is returned to the user that the transmission was successful. The captured images may be automatically deleted after successful transfer. If the download is unsuccessful, a notification such as, e.g., a text message or prompt from the mobile device is provided to the user. The document images that have not been transferred can be retained on the mobile device for subsequent transfer.

Figure 1A:
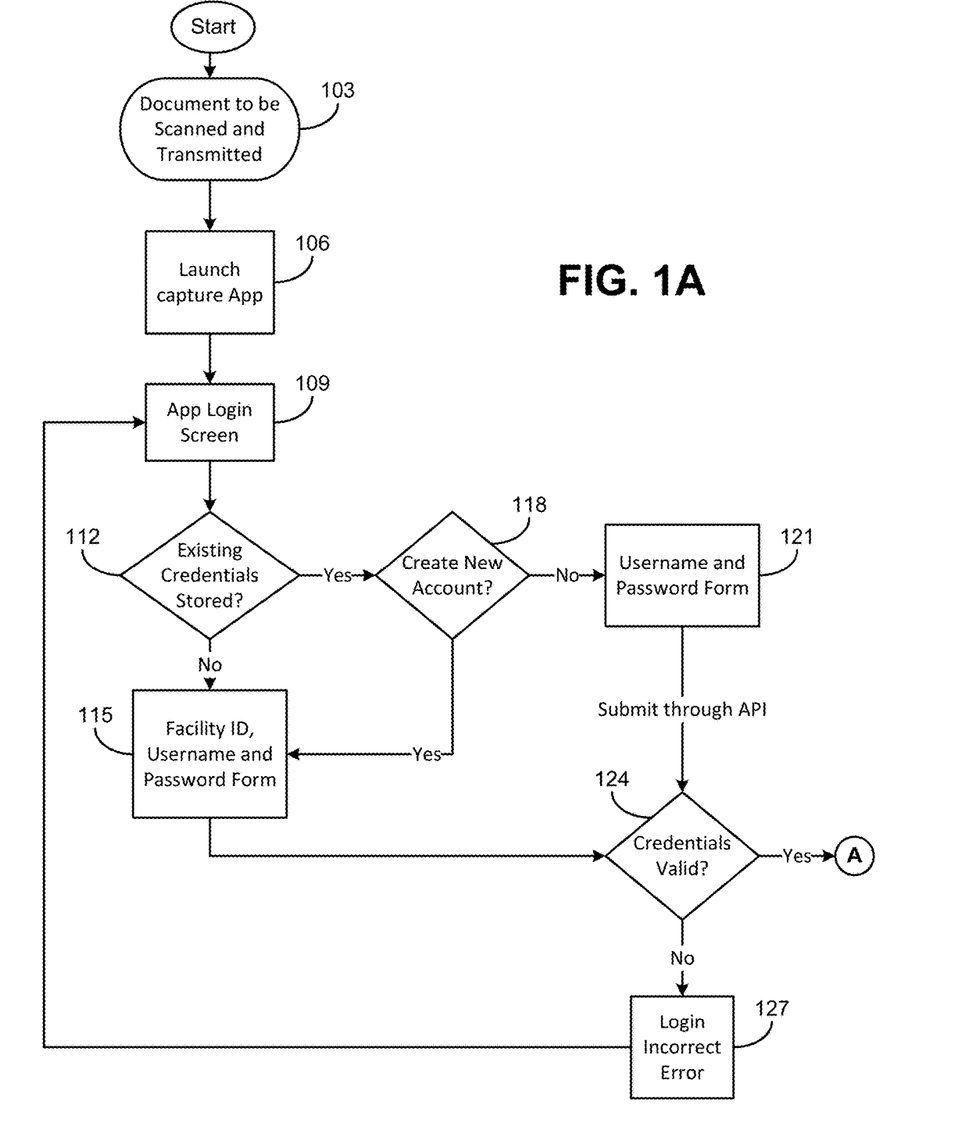
FIGS. 1A and 1B are a flowchart of an example of image capture and transmission of a document to a secure repository in accordance with various embodiments of the present disclosure.
Figure 1B:
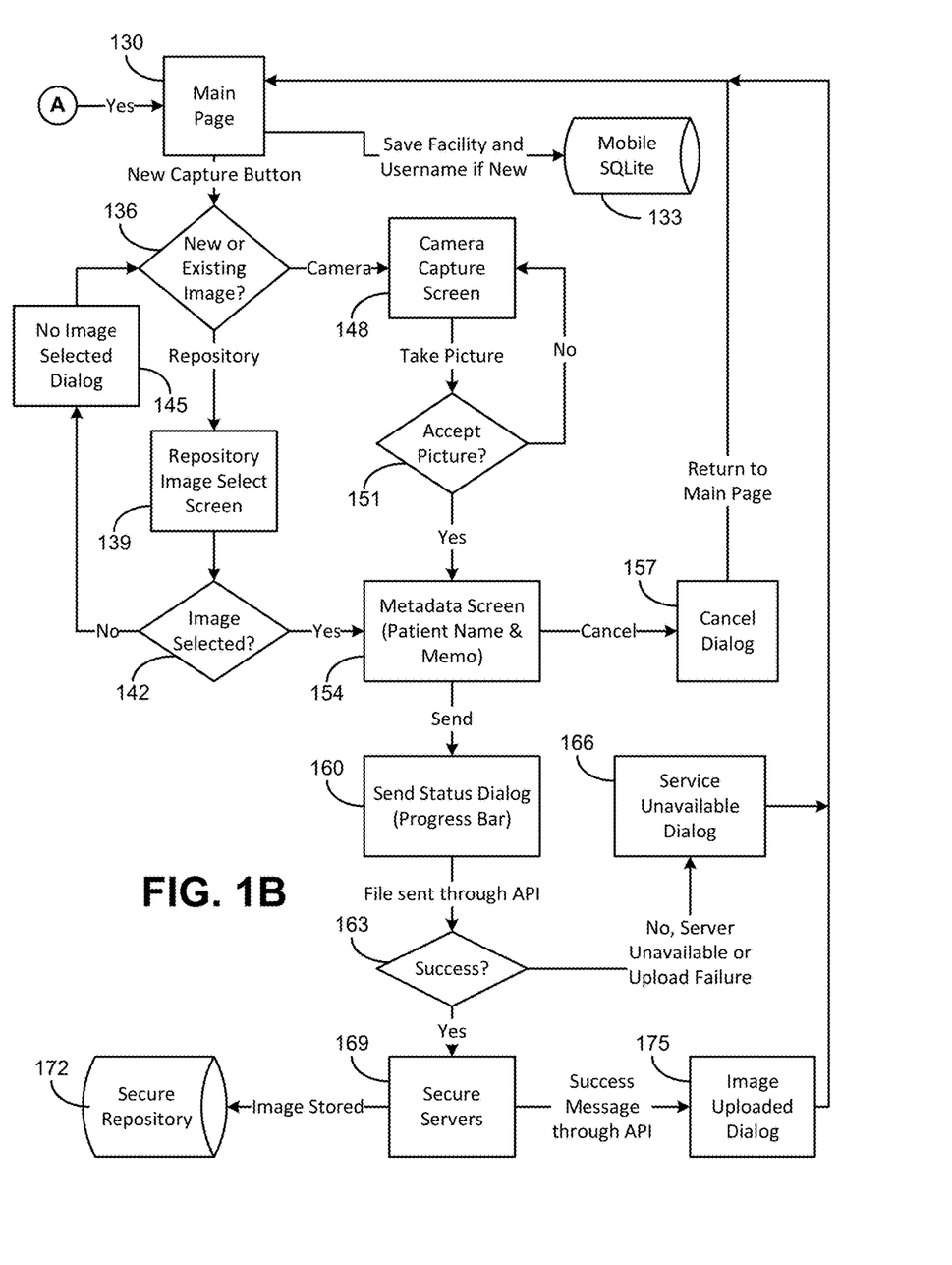
Figure 2A:
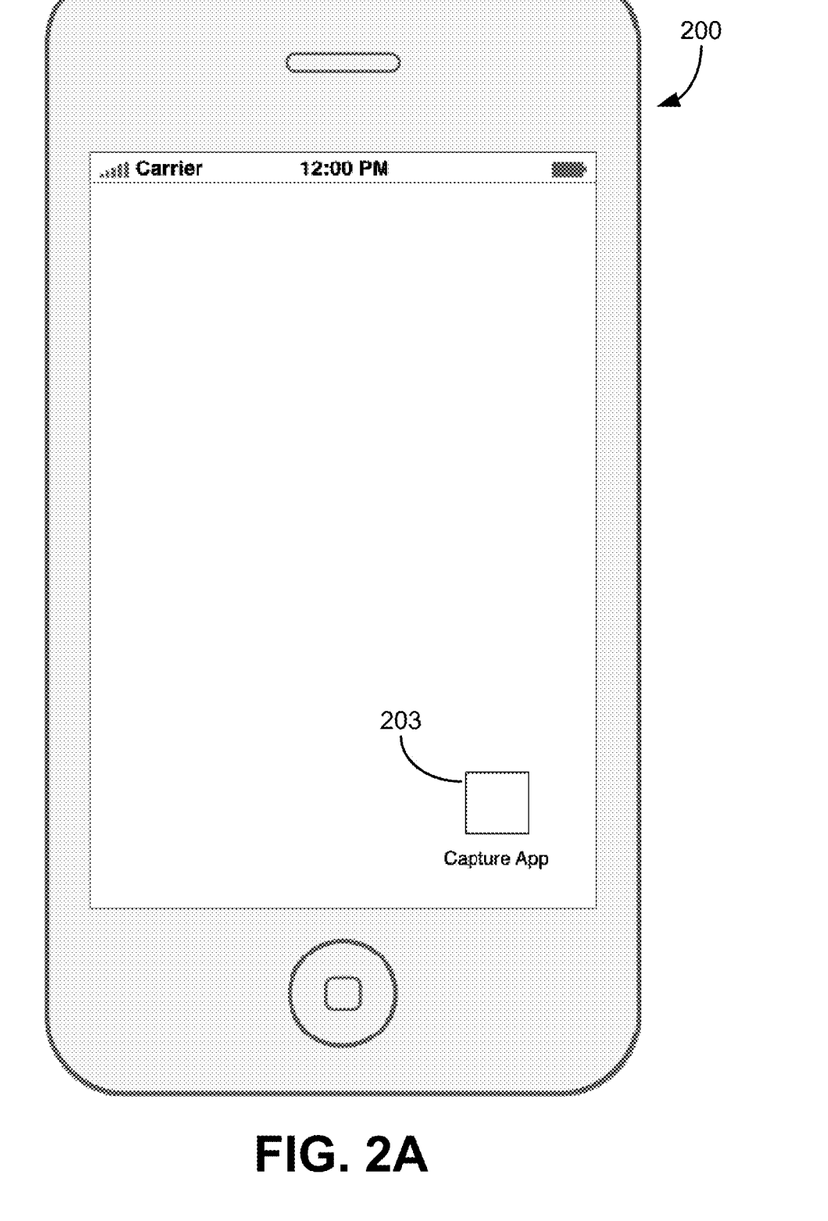
FIGS. 2A through 2H are examples of a mobile device display during the image capture and transmission of FIGS. 1A and 1B in accordance with various embodiments of the present disclosure.
Figure 2B:
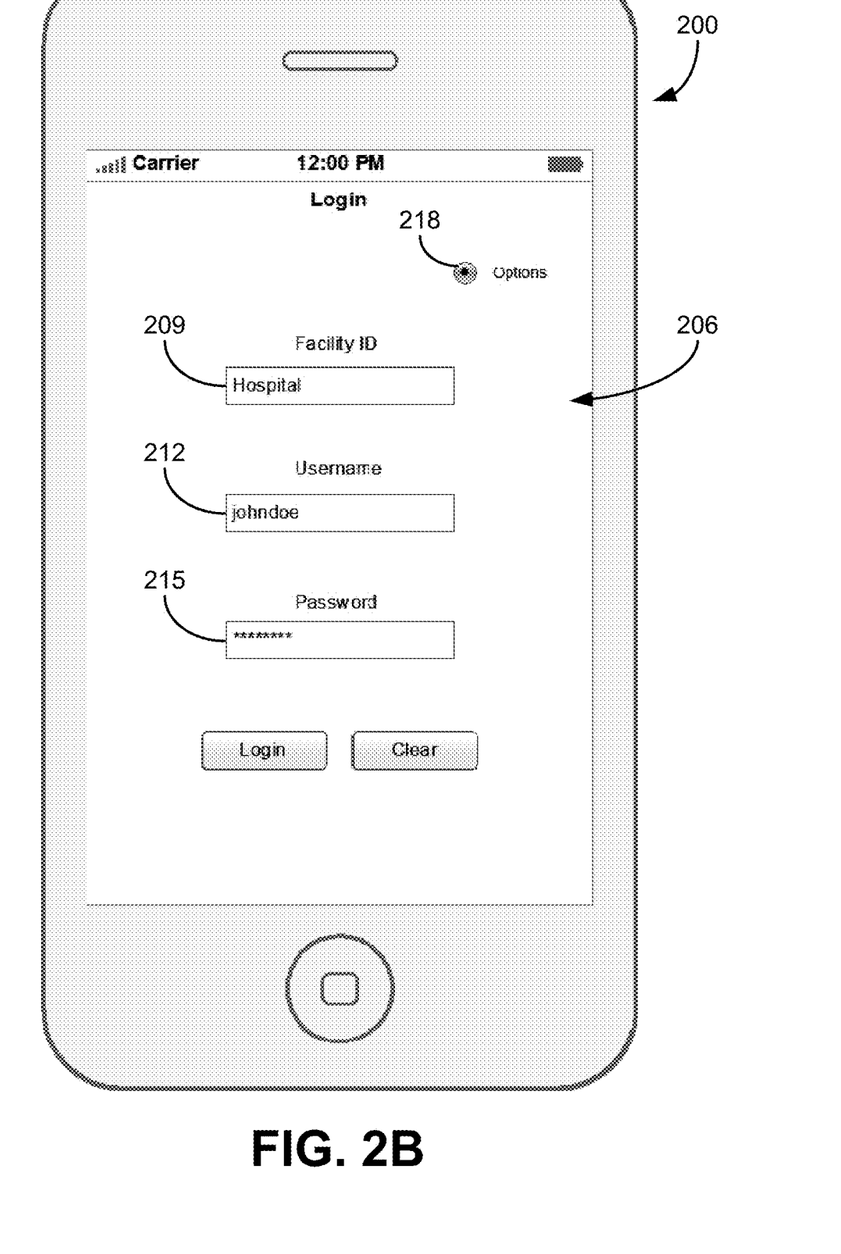

Other features and advantages of the present disclosure should become apparent from the following description of an example of the capture and secure transmission of document images, taken in conjunction with the flowchart of FIGS. 1A and 1B, which illustrate, by way of example, the principles of the disclosure. Referring to FIG. 1A, shown is a first portion of the flowchart 100. Beginning with block 103, the user obtains a document for scanning and transmission to the secure repository. The user may launch the application (or "app") on the mobile device in block 106. FIG. 2A illustrates a mobile device 200 with an example of an icon or "button" 203 rendered on the display, which may be selected by the user to initiate the application. When the application is launched, a login screen is presented on the mobile device 200 in block 109 to verify the identity of the user. FIG. 2B illustrates the mobile device 200 with an example of a login screen 206 rendered on the display. The login screen 206 may allow for entering user identification information or credentials such as, e.g., a Facility ID (identification) 209, a Username 212 and/or a Password 215. Various options may also be initiated from the login screen 206 by, e.g., selecting an options icon 218. For example, in block 112 of FIG. 1A an option may be presented on the mobile device display which allows the credentials of a user to be stored to facilitate future access to the scanned and/or stored documents by the user. If the option to save the credentials on the mobile device 200 is not selected in block 112, the user enters identification information or credentials such as, e.g., the Facility ID 209, Username 212 and/or Password 215 in block 115.

If the user's credentials differ from the previously stored credentials, the user may create a new account in block 118 by selecting a "new account" button or icon that may be rendered on the display of the mobile device 200. If the displayed credentials match the current user's credentials, the user can authenticate his or her identity in block 121 using, e.g., the appropriate username and password combination, finger-swipe pattern, voice recognition, biometric information (e.g., fingerprint or eye scan), or other form of authentication. In block 124, the credentials can be transmitted to a remote authentication server using an SSL-encrypted secure channel for verification. If the credentials do not match the stored credentials on the remote authentication server in block 127, then an invalid login message is returned to the application over the secure SSL channel and the application returns to the login screen in block 109.

Figure 2C:
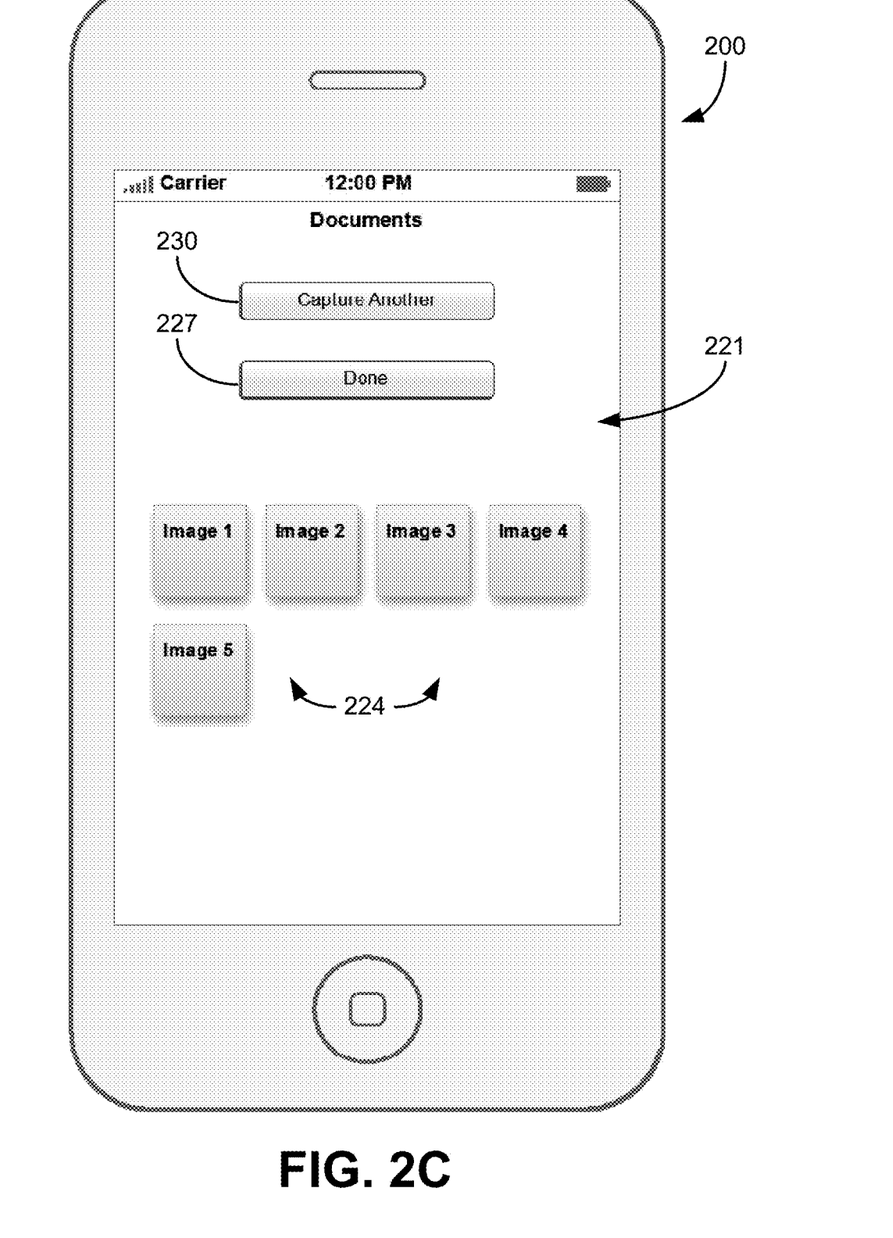

Referring now to FIG. 1B, if the credentials match the remote authentication server credentials for the user, then the main page is displayed on the mobile device 200 in block 130. When a new account has been indicated, the Facility ID 209, Username 212, and/or other user settings may be stored in a local database or memory of the mobile device 200 in block 133. From the main (or menu) page of block 130, the user can select a "new capture" button or icon rendered on the mobile device 200 to obtain a document image. In block 136, the user may be offered the option of capturing a new image or selecting a file from a secure data store (or repository) on the mobile device 200. If the user chooses to obtain a document image from the secure local data store, a select dialog screen displaying thumbnails or other listing of document images awaiting transmittal is shown in block 139. FIG. 2C illustrates the mobile device 200 with an example of a select dialog screen 221 rendered on the display including a plurality of thumbnails of the stored document images 224. The user may then select one or more documents 224 in block 142 of FIG. 1B for secure transmittal to the remotely located secure repository. When the user completes his or her selection, a cancel or "done" button or icon 227 (FIG. 2C) may be selected. If the cancel or "done" button or icon 227 is "clicked" without the selection of a document 224, the application may provide a "no image selected" confirmation in block 145 and the user is returned to block 136 where the user may again be offered the option of capturing a new image or selecting a file from the secure data store (or repository). In the select dialog screen 221 of FIG. 2C, the user is offered the option to capture another image by selecting a "capture another" button or icon 230.

Figure 2D:
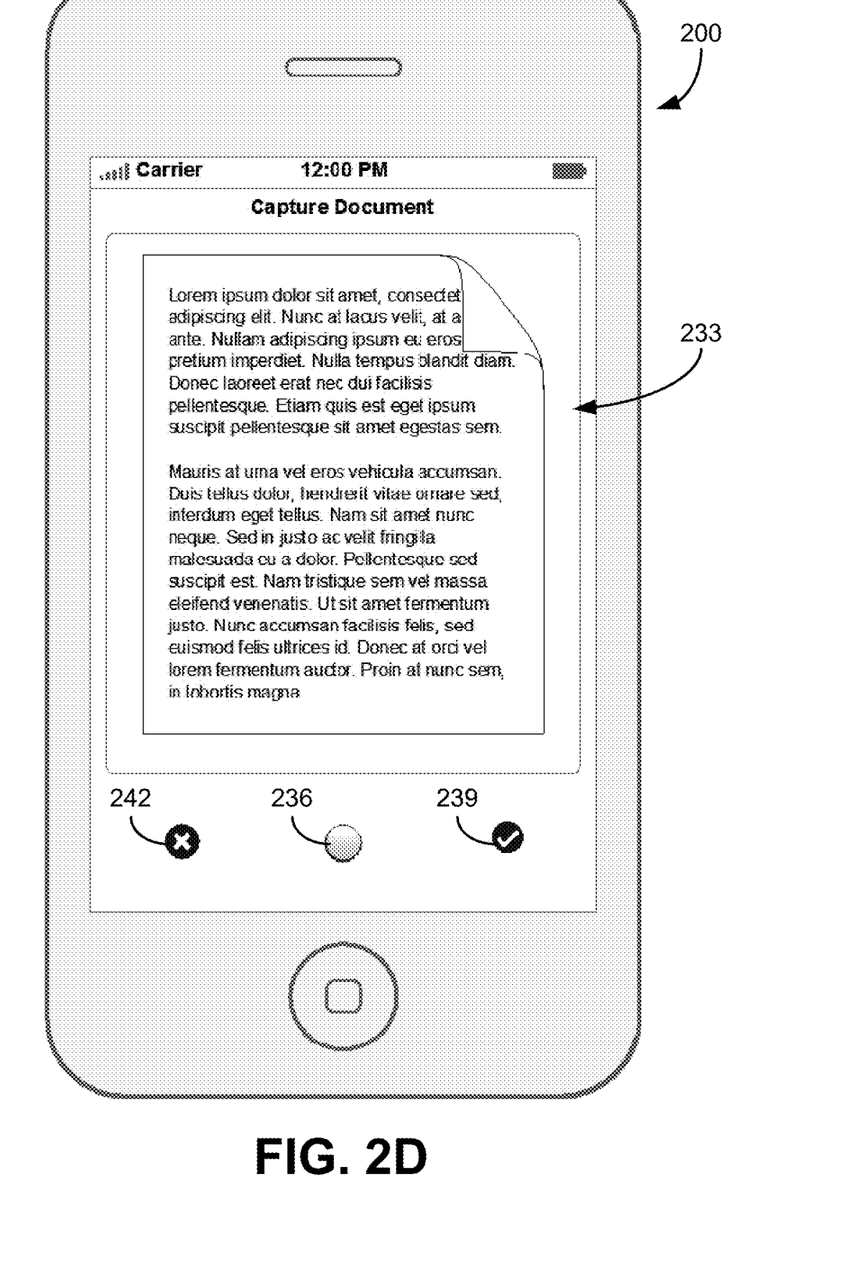

If the camera capture option is selected in block 136, the mobile device provides the user with a camera capture screen in block 148. FIG. 2D illustrates the mobile device 200 with an example of a camera capture screen 233 rendered on the display. The camera capture screen 233 may include a viewfinder with a select button or icon 236. The user adjusts the mobile device until the document to be captured is fully in the frame and in focus and takes the picture by "clicking" the select button 236. The capture screen 233 may include image boundary markers such as, e.g., brackets in the corners of the capture screen 233 to delineate the edges of the captured image. The capture screen 233 may also include other icons for controlling camera features such as, e.g., flash control and contrast. In some implementations, the mobile device 200 may automatically detect the document within the image and geometrically correct the image, binarize the image, correct the orientation of the image, and/or correct the size of the image. The captured image is displayed in the viewfinder and the user can select an accept button or icon 239 or a cancel button or icon 242 in block 151 of FIG. 1B. If the captured image is not accepted in block 151, then the application returns to the camera capture screen 233 (FIG. 2C) in block 148.

Figure 2E:
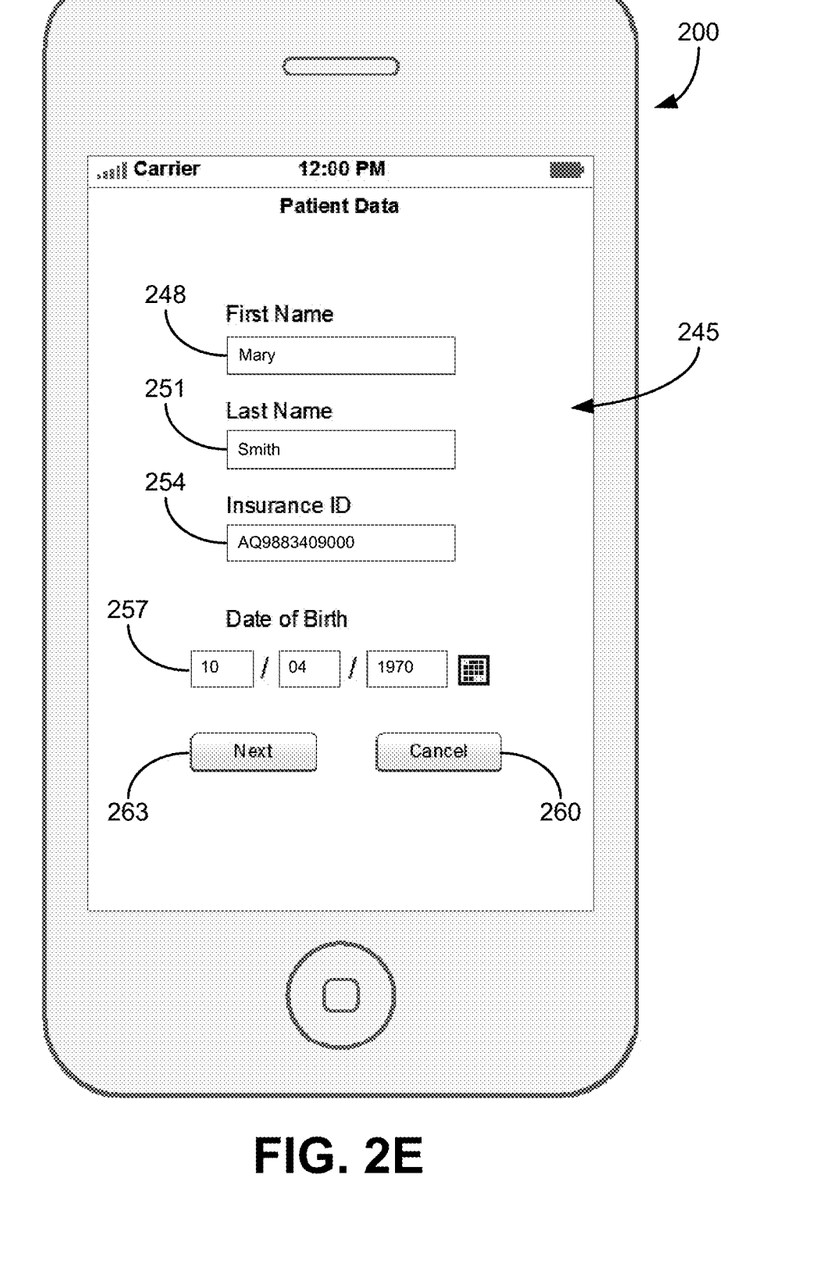
Figure 2F:
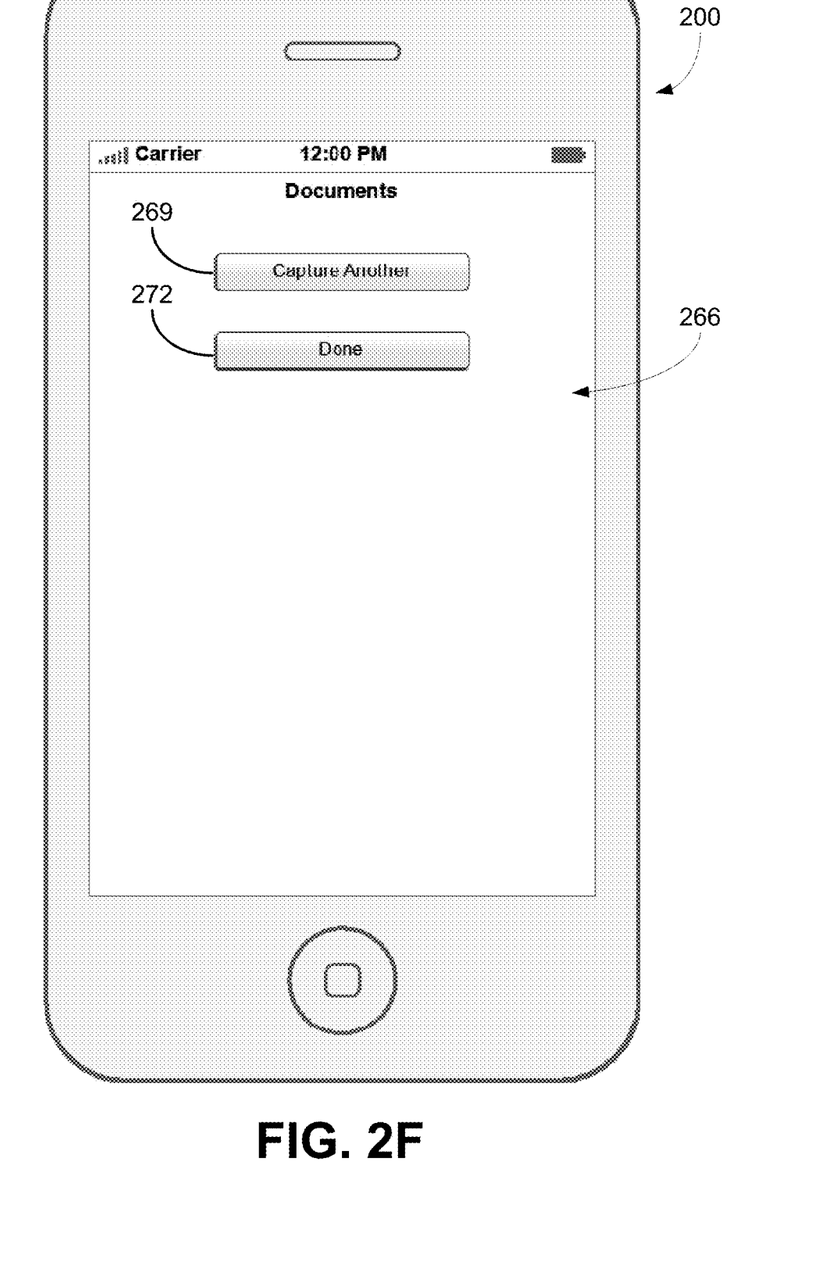

If the captured image is accepted in block 151, the application may display a metadata screen to obtain additional document information in block 154 of FIG. 1B. FIG. 2E illustrates the mobile device 200 with an example of a metadata screen 245 rendered on the display. The additional data may include the first name 248, last name 251, insurance identification 254, date of birth 257, or other information associated with the patient of the document. For example, the metadata screen 245 may include areas to add a description and/or comments regarding the image. A warning message may be provided to the user if no data has been entered to identify the image. If the user selects the "cancel" button or icon 260, the application provides a cancellation indication in block 157 of FIG. 1B and the user is returned to the main page in block 130. If the additional data is entered by selecting the "next" button or icon 263 in FIG. 2E, the application may prompt the user to determine if an additional image should be captured. FIG. 2F illustrates the mobile device 200 with an example of a capture prompt screen 266 rendered on the display, which provides the option to capture another image by selecting a "capture another" button or icon 269 or complete the image capture by selecting a "done" button or icon 272. The application may allow multiple document images to be captured by the mobile device 200 before secure transmission to the remotely located secure repository. Referring back to FIG. 1B, when the user enters the metadata associated with the document(s), the user can initiate transmission by selecting a "send" button or icon in block 160.

When an image is captured, the image file is saved in a private mode (MODE_PRIVATE) where only the application has access to the image file. The image file(s) can be maintained in a directory that is restricted to the application such that the user will not have access to the file system and/or image file. Access to the directory from outside of the application is excluded. Document information such as identifying information, descriptions and/or comments supplied by the user is also stored in the application specific directory. The image file(s) can be stored in the application specific directory until it is sent to the secure repository or the user no longer has access to the directory. For example, the user can lose access by a crash or power down of the application and/or mobile device 200 or a home key close or logout by the user may cashed the image file(s) for later access.

If the application and/or mobile device 200 crashes or powers down, then all references to the image files are lost. The image data will be removed from memory because the image data only exists within the running application. Selection of a home key (button or icon) may remove the application from the foreground or may close the application. If the application closes, then the image file(s) are removed. If selecting the home key simply removes the application from the foreground of the mobile device, then the image file(s) are retained for later access. Logout by the user deletes the document information (or data), but does not remove the images. In that case, the image file(s) can be deleted after logging back in and sending the image file(s) to the secure repository. When the application is uninstalled from the mobile device 200, all data and image files associated with application will be removed from the mobile device 200.

Although the flow chart of FIGS. 1A and 1B shows a specific order of execution, the order of execution may differ from that which is depicted. For example, after the user's identity is verified through the login screen, the user may be able to select between securely transmitting one or more document image to the remotely located secure repository or to logout or exit the application from the main (or menu) page. When sending to the repository is selected, a metadata screen may be presented that is configured to allow the user to enter identifying information, descriptions and/or comments regarding the document image that will be captured. If no data is entered by the user before continuing to image capture, a warning message may be presented. For example, the warning message may indicate the benefit of adding information for subsequent identification of the image. The warning message may include the ability to return to the metadata screen to enter data or proceed without user provided information. If a group of document images are captured together, the identifying information, description and/or comments may be applied to all images of the group. Information for each document image may be subsequently edited.

A camera capture screen may then be provided to capture a document image. The capture screen may include image boundary markers such as, e.g., brackets in the corners of the camera capture screen to delineate the edges of the captured image. A button or icon may be presented on the camera capture screen to initiate image capture by the user. The camera capture screen may also include icons for controlling camera features such as, e.g., turning on or off the camera flash, adjusting image contrast, or selecting capture of color or black/white images. The captured document image may then be displayed (e.g., in a preview screen) with options to retake or accept the captured image. By selecting a "retake" button or icon, the user is returned to the camera capture screen. The user may accept the captured image by selecting a "done" button or icon.

Once the image has been accepted, the application may prompt the user to determine if an additional image should be captured. For example, a capture prompt screen may be rendered on the display that provides the option to capture another document image by selecting an "capture another" or "add image" button or icon. The capture prompt screen may also include an option to edit the identifying information, descriptions and/or comments associated with the document image. In some embodiments, a listing of the document images transferred to the secure repository may be displayed with, e.g., user name, creation date, etc. to allow selection for editing the data. The image capture may be completed by selecting a button or icon to initiate sending the image(s) to the secure repository.

Figure 2G:
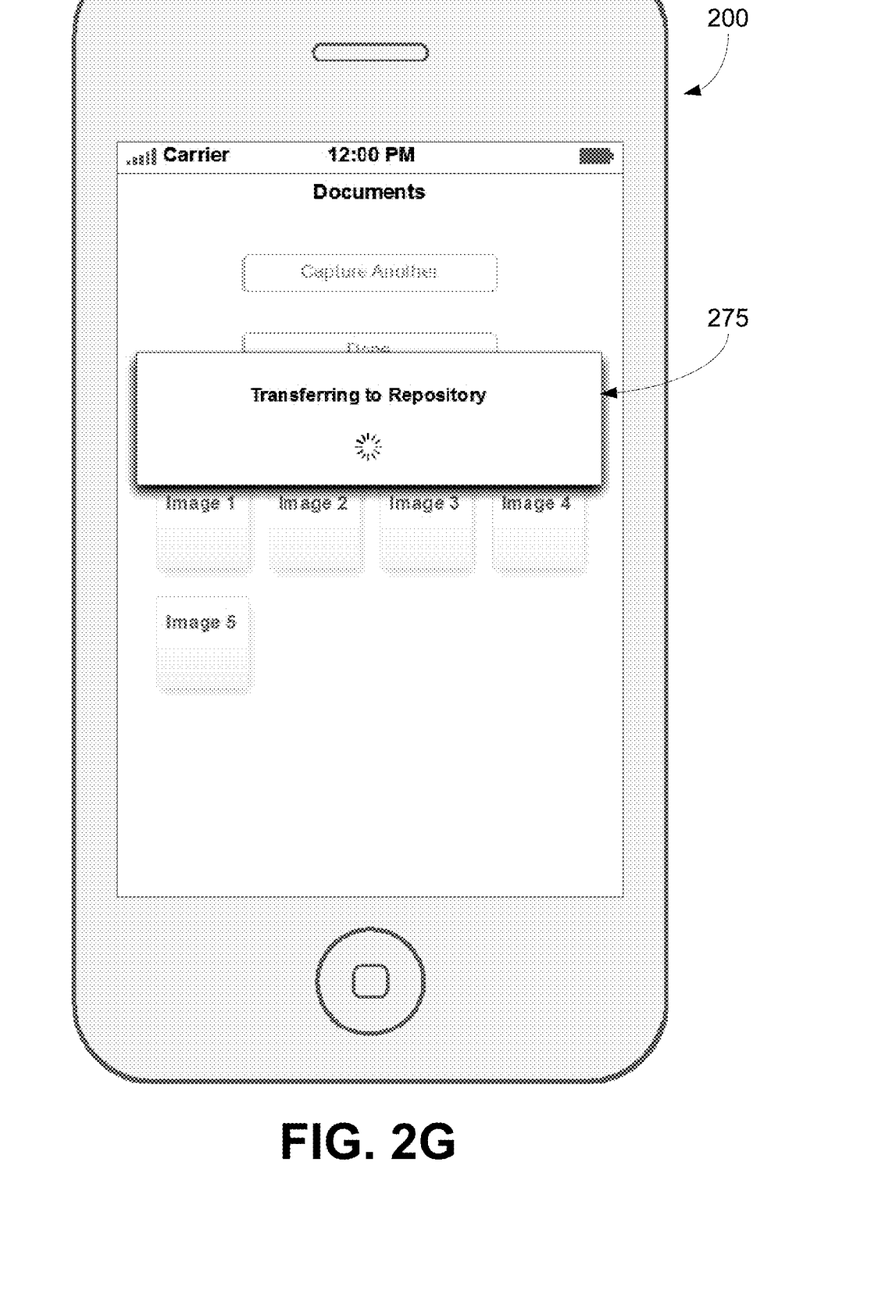
Figure 2H:
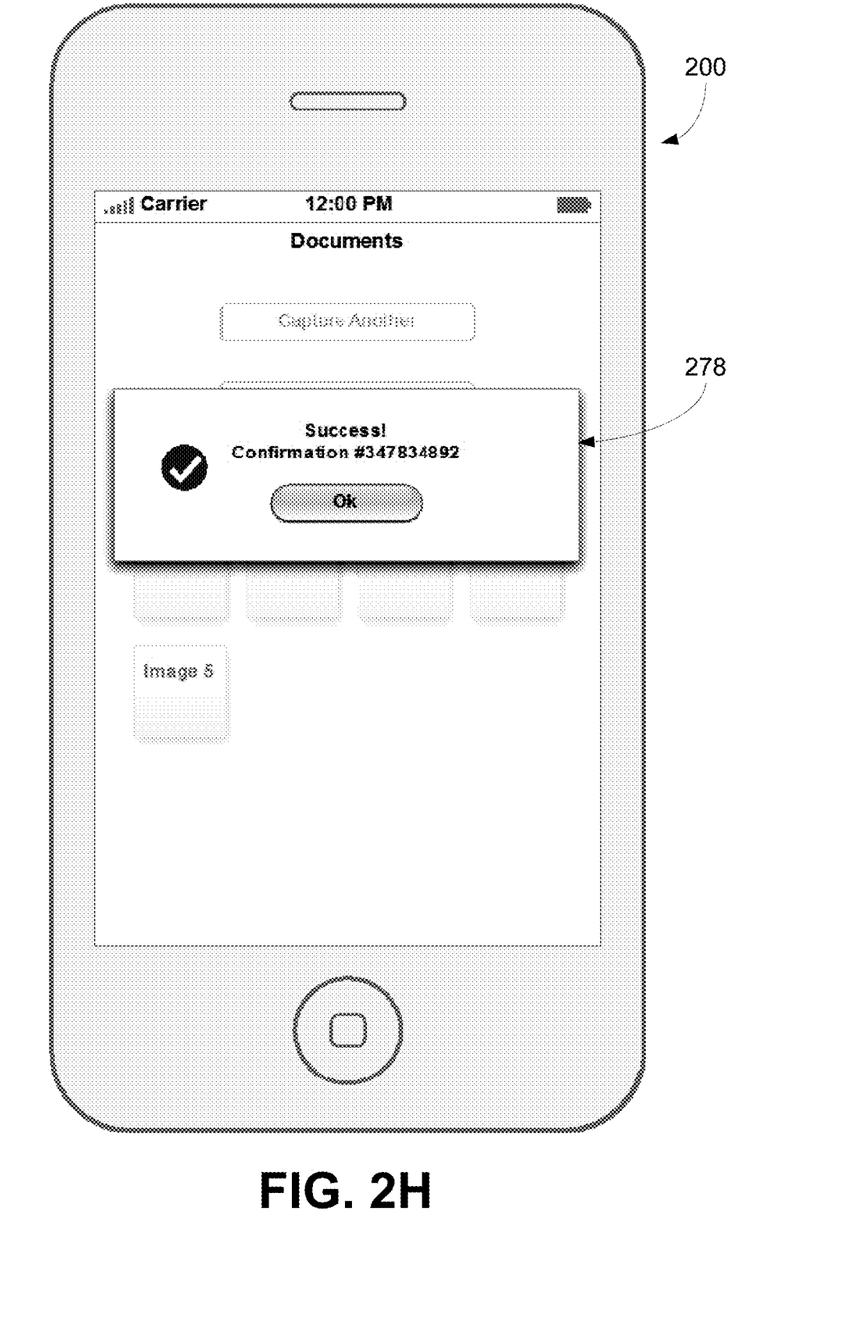

Referring back to FIG. 1B, the user can initiate transmission by selecting a "send" button or icon in block 160. The application checks for an active connection such as, e.g., a active TCP/IP connection in block 163 and if one is available, the documents can be sent as a secure message over SSL and the progress bar (or other indication) is displayed. FIG. 2G illustrates the mobile device 200 with an example of a transfer progress bar 275 rendered on the display. If a connection is not available in block 163 of FIG. 1B, the application may notify the user that service is unavailable in block 166. In some implementations, the application may prompt to see if the availability of an active TCP/IP connection should be reconfirmed before returning to the main page in block 130. Once the progress bar reaches 100% in block 163, a success or failure message can be transmitted from the remote secure server to the app. If the upload failed, a notification is provided to the user in block 166 and the application can return to the main page in block 130. If the secure transfer to the secure servers was successful in block 169, copies of the transferred documents may be distributed in block 172 to multiple databases within the secure repository for redundancy. The captured images may be automatically deleted from the mobile device 200 after successful transfer. Once a document is stored securely, a message can be sent in block 175 by the remote server and displayed to the user on the mobile device 200 or through other appropriate notification avenues in block 172 before returning to the main page in block 130. FIG. 2H illustrates the mobile device 200 with an example of a transfer confirmation 278 rendered on the display. The transfer confirmation may include confirmation identification information for later reference.

Figure 3:
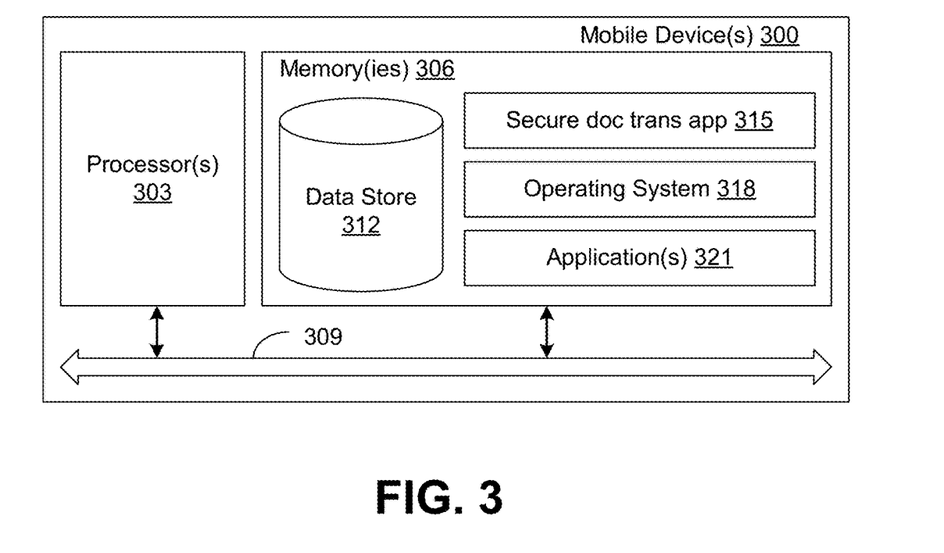
FIG. 3 is a schematic block diagram that provides one example illustration of a mobile device in accordance with various embodiments of the present disclosure.

With reference now to FIG. 3, shown is a schematic block diagram of a mobile device 300 that may be used to implement automated document capture and secure transmittal according to various embodiments of the present disclosure. The mobile device 300 includes at least one processor circuit, for example, having a processor 303 and a memory 306, both of which are coupled to a local interface 309. To this end, the mobile device 300 may comprise, for example, at least one smart phone, tablet, computer, or like device. The local interface 309 may comprise, for example, a data bus with an accompanying address/control bus or other bus structure as can be appreciated. The mobile device 300 includes a display for rendering of generated graphics such as, e.g., a user interface and an input interface such, e.g., a touch screen to allow for user input. In addition, the mobile device 300 includes communication interfaces (not shown) that allow the mobile device 300 to communicatively couple with other devices such as, e.g., components of a communication network. The communication interfaces may include one or more wireless connection(s) such as, e.g., Bluetooth or other radio frequency (RF) connection and/or one or more wired connection(s).

Stored in the memory 306 are both data and several components that are executable by the processor 303. The memory 306 may include a data store 312, which may be capable of secure encrypted storage of data. In particular, stored in the memory 306 and executable by the processor 303 are a secure document capture and transmission application 315, an operating system 318, and/or other applications 321. It is understood that there may be other applications that are stored in the memory 306 and are executable by the processor 303 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 306 and are executable by the processor 303. In this respect, the term "executable" means a program file that is in a form that can ultimately be run by the processor 303. Examples of executable programs may be, for example, a compiled program that can be translated into machine code in a format that can be loaded into a random access portion of the memory 306 and run by the processor 303, source code that may be expressed in proper format such as object code that is capable of being loaded into a random access portion of the memory 306 and executed by the processor 303, or source code that may be interpreted by another executable program to generate instructions in a random access portion of the memory 306 to be executed by the processor 303, etc. An executable program may be stored in any portion or component of the memory 306 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 306 is defined herein as including both volatile and nonvolatile memory and data storage components. Volatile components are those that do not retain data values upon loss of power. Nonvolatile components are those that retain data upon a loss of power. Thus, the memory 306 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 303 may represent multiple processors 303 and the memory 306 may represent multiple memories 306 that operate in parallel processing circuits, respectively. In such a case, the local interface 309 may be an appropriate network that facilitates communication between any two of the multiple processors 303, between any processor 303 and any of the memories 306, or between any two of the memories 306, etc. The local interface 309 may comprise additional systems designed to coordinate this communication, including, for example, performing load balancing. The processor 303 may be of electrical or of some other available construction.

Although the secure document capture and transmission application 315, the operating system 318, application(s) 321, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flow chart of FIGS. 1A and 1B shows the functionality and operation of an implementation of portions of the secure document capture and transmission application 315. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 303 in a computer system or other system. The machine code may be converted from the source code, etc. If embodied in hardware, each block may represent a circuit or a number of interconnected circuits to implement the specified logical function(s).

Although the flow chart of FIGS. 1A and 1B shows a specific order of execution, it is understood that the order of execution may differ from that which is depicted. For example, the order of execution of two or more blocks may be scrambled relative to the order shown. Also, two or more blocks shown in succession in FIGS. 1A and 1B may be executed concurrently or with partial concurrence. Further, in some embodiments, one or more of the blocks shown in FIGS. 1A and 1B may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the secure document capture and transmission application 315 and/or application(s) 321, that comprises software or code can be embodied in any non-transitory computer-readable medium for use by or in connection with an instruction execution system such as, for example, a processor 303 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method for secure capture and transmission of a file to a secure repository on a server, comprising:
   providing access to a secure document capture interface on a mobile device in response to verification of user credentials by a remote authentication server;
   capturing an image of a document through the secure document capture interface, the image captured as an image file using a camera of the mobile device;
   generating, by the mobile device, an updated image file by adding metadata to the image file, the metadata entered through the secure document capture interface;
   storing the updated image file in encrypted secure memory of the mobile device, where access to the updated image file stored in the encrypted secure memory is restricted to the secure document capture interface on the mobile device;
   establishing a secure encrypted connection to the server in response to a user command to save the updated image file, wherein the secure encrypted connection is a secure connection over a wireless link, and the user command is provided through the secure document capture interface;
   transmitting, by the mobile device, the updated image file securely to the server, where the updated image file is transmitted via the secure encrypted connection and stored in the secure repository on the server;
   receiving confirmation of successful transfer of the updated image file to the server; and
   automatically removing, by the mobile device, the updated image file from the encrypted secure memory of the mobile device in response to receiving the confirmation.

2. The method of claim 1, wherein the capturing of the image of the document comprises:
   capturing a first image of the document using the mobile device;
   automatically detecting, by the mobile device, the document within the first image;
   generating a corrected first image by geometrically correcting the first image; and
   outputting the corrected first image as the image of the document.

3. The method of claim 2, comprising binarizing the first image.

4. The method of claim 2, comprising correcting an orientation of the first image.

5. The method of claim 2, comprising correcting a size of the first image.

6. The method of claim 1, wherein the secure encrypted connection is a SSL connection over a wireless link.

7. The method of claim 1, further comprising:
   capturing an image of a second document through the secure document capture interface, the image of the second document captured as a second image file using the camera of the mobile device;
   generating a second updated image file by adding metadata to the second image file; and
   transmitting the second updated image file securely to the server via the secure encrypted connection.

8. The method of claim 7, further comprising storing the second updated image file in the encrypted secure memory of the mobile device, where access to the second updated image file stored in the encrypted secure memory is restricted to the secure document capture interface.

9. A mobile device, comprising:
   processing circuitry and memory; and
   a secure transfer application stored in the memory for secure capture and transmission of a file from the mobile device to a secure repository on a server, where the secure transfer application, when executed by the processing circuitry, causes the mobile device to:
   provide access to a secure document capture interface on the mobile device in response to remote server authentication of user credentials;
   capture an image of a document in response to a user input provided through the secure document capture interface, the image captured as an image file;
   generate an annotated image file by adding metadata to the image file, the metadata provided through the secure document capture interface;
   store the annotated image file in encrypted secure memory of the mobile device, where files stored in the encrypted secure memory are accessible only through the secure transfer application;
   establish a secure encrypted connection to the server in response to a user command to save the annotated image file, wherein the secure encrypted connection is a secure connection over a wireless link, and the user command is provided through the secure document capture interface;

transmit the annotated image file including the metadata to the server via the secure encrypted connection, where the server stores the annotated image file including the metadata in the secure repository;

receive confirmation of successful transfer of the annotated image file to the server; and automatically remove the annotated image file from the encrypted secure memory of the mobile device in response to receiving the confirmation.

10. The mobile device of claim 9, wherein the mobile device receives the confirmation of successful transfer from the server via the secure encrypted connection.

11. The mobile device of claim 9, wherein the secure transfer application causes the mobile device to display a failure notification via the secure document capture interface in response to a failed upload of the annotated image file to the server.

12. The mobile device of claim 9, wherein the secure transfer application causes the mobile device to display a failure notification via the secure document capture interface in response to a failure to establish the secure encrypted connection to the server.

13. The mobile device of claim 9, wherein the secure transfer application causes the mobile device to:

capture images of a plurality of documents as image files in response to user inputs provided through the secure document capture interface;

generate annotated image files by adding metadata to the image files; and transmit the annotated image files to the server via the secure encrypted connection.

14. A non-transitory computer-readable medium embodying a program executable in a mobile processing device, the program for secure capture and transmission of a file from the mobile processing device to a secure repository on a server, the program comprising instructions that cause the mobile processing device to:

provide a secure document capture interface on the mobile processing device in response to remote server authentication of a user;

capture an image of a document in response to a capture command provided through the secure document capture interface, the image captured as an image file;

generate an annotated image file by adding metadata to the image file;

store the annotated image file in encrypted secure memory of the mobile processing device, where files stored in the encrypted secure memory are accessible only through the secure document capture interface;

establish a secure encrypted connection to the server in response to a user command to save the annotated image file, wherein the secure encrypted connection is a secure connection over a wireless link, and the user command is provided through the secure document capture interface;

transmit the annotated image file including the metadata securely to the server via the secure encrypted connection, where the server is configured to store the annotated image file including the metadata in the secure repository;

receive confirmation of successful transfer of the annotated image file to the server; and automatically remove, the annotated image file from the encrypted secure memory of the mobile processing device in response to receiving the confirmation.

15. The non-transitory computer-readable medium of claim 14, wherein the program causes the mobile processing device to:

capture images of a plurality of documents as image files in response to user input capture commands provided through the secure document capture interface:

store annotated image files in the encrypted secure memory, where the annotated image files are generated by adding metadata provided through the secure document capture interface to the image files;

transmit the annotated image files to the server via the secure encrypted connection: and remove the annotated image files from the encrypted secure memory in response to confirmation of successful transfer of the annotated image files to the server.

* * * * *